(12) United States Patent
Pagano (10) Patent No.: US 8,758,416 B2
(45) Date of Patent: Jun. 24, 2014

(54) ODONTOID FRACTURE DYNAMIC COMPRESSION APPARATUS AND METHOD

(76) Inventor: Paul J. Pagano, Canfield, OH (US)

( * ) Notice: Subject to any disclaimer, the term of this patent is extended or adjusted under 35 U.S.C. 154(b) by 432 days.

(21) Appl. No.: 12/971,181

(22) Filed: Dec. 17, 2010

(65) Prior Publication Data

US 2011/0224735 A1    Sep. 15, 2011

Related U.S. Application Data

(60) Provisional application No. 61/312,377, filed on Mar. 10, 2010, provisional application No. 61/312,957, filed on Mar. 11, 2010.

(51) Int. Cl.
*A61B 17/80* (2006.01)
(52) U.S. Cl.
USPC .......................... 606/286; 606/280; 606/291
(58) Field of Classification Search
USPC .......................... 606/280, 286, 291
See application file for complete search history.

(56) References Cited

U.S. PATENT DOCUMENTS

| | | | |
|---|---|---|---|
| 5,318,567 A | | 6/1994 | Vichard |
| 5,810,821 A | * | 9/1998 | Vandewalle ............... 606/65 |
| 6,129,730 A | * | 10/2000 | Bono et al. ............... 606/291 |
| 6,579,290 B1 | | 6/2003 | Hardcastle et al. |
| 2004/0153078 A1 | | 8/2004 | Grinberg |

FOREIGN PATENT DOCUMENTS

EP    1306058 A2    5/2003

OTHER PUBLICATIONS

International Search Report for International Application No. PCT/US2011/027898, dated Jul. 8, 2011.

* cited by examiner

*Primary Examiner* — Nicholas Woodall
(74) *Attorney, Agent, or Firm* — Renner, Otto, Boisselle & Sklar, LLP.

(57) ABSTRACT

A cervical fixation system and method for repairing odontoid fractures includes securing an anterior plate to caudal portion of C2 body below the odontoid neck. The anterior plate houses lag screw within a posterior shaft. A cannulated fixation device crosses the fracture site with fixation into the cephalad fragment. The lag screw can be pulled caudally into the plate with a compression screw to apply a compression force across the fracture site.

13 Claims, 13 Drawing Sheets

Type-2 Odontoid Fracture

108 — Compression Screw With Head

Figure 20B

ODONTOID FRACTURE DYNAMIC COMPRESSION APPARATUS AND METHOD

RELATED APPLICATION DATA

The present application claims the benefit of the filing date of U.S. Provisional Patent Application Ser. Nos. 61/312,377 filed Mar. 10, 2010 and 61/312,957 filed Mar. 11, 2010, which are incorporated herein by reference.

TECHNICAL FIELD OF THE INVENTION

The technology of the present disclosure relates to the orthopedic field of fracture fixation, and more particularly to fixation of vertebrae bodies in the cervical spine.

BACKGROUND

A fractured bone generally must be kept together for lengthy periods of time in order to permit the recalcification and bonding of the fractured portions of the bone. Accordingly, adjoining portions of a fractured bone typically are clamped together or attached to one another by means of a pin or a screw driven through the rejoined portions. Fixation of spinal fractures raises a host of special problems due to the location of the bones, the impact of the injury on the patient, rehabilitation, quality of life issues, etc.

SUMMARY

The present disclosure overcomes many drawbacks associated with the repair of conventional spinal fractures. An anterior plate and lag screw dynamic fixation device specifically for odontoid fractures is disclosed herein. The anterior plate is applied to a caudal portion of the second cervical vertebrae body (C2) below the odontoid neck. The anterior plate houses a cannulated lag screw within a posterior shaft. The cannulated lag screw crosses the fracture site with fixation into cephalad fragment. The lag screw can be pulled caudally into the plate with a compression screw housed within and/or secured within the posterior shaft to apply a compression force across the fracture site.

One aspect of the invention is directed to a cervical fixation system including: a plate having a surface for fixation to a cervical body surface, wherein the plate includes a plurality of voids formed in the plate, wherein the voids are positioned to allow fixation of the plate to the cervical body and the plate further includes a shaft coupled to a posterior surface of the plate; a first fastening device and a second fastening device, wherein the first and second fastening devices are configured to be received by one or more voids formed in the plate, wherein the fastening devices secure the plate to the cervical body surface; and a fixation device configured to be housed in the shaft, wherein the fixation device is configured to be secured across at least a portion of the cervical body and an odontoid associated with the cervical body and the fixation device includes a compression screw to apply a compression force across at least a portion of the cervical body and an odontoid associated with the cervical body.

Another aspect of the invention relates to a method including: exposing at least a portion of a cervical spine of an associated patient; forming a void into at least a portion a second cervical (C2) body and an odontoid; placing a guide wire through a portion of the C2 body cephalad into the odontoid; placing a cannulated lag screw into the odontoid over the guide wire; placing an anterior plate onto a inferior surface of the C2 body, wherein the plate includes a plate surface configured to be secured to at least a portion of a surface of the C2 body surface of the associated patient's cervical spine, wherein the plate includes a plurality of voids formed in the plate, wherein the voids are positioned to allow fixation of the plate to the cervical body and the plate further includes a shaft coupled to a posterior surface of the plate, wherein the anterior plate is placed in such a manner to have the cannulated lag screw aligned with the shaft; securing the anterior plate to the C2 body through the one or more the voids with one or more fastening devices; and applying a compressive force from a compression screw threaded into an inferior shaft of the lag screw, wherein as a head of the compression screw contacts an inferior edge of the anterior plate, the lag screw is pulled in a caudal direction through the shaft to apply a compressive force across the odontoid fracture with the C2 body.

These and further features will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the scope of the claims appended hereto.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, integers, steps or components but does not preclude the presence or addition of one or more other features, integers, steps, components or groups thereof.

Many aspects of the invention can be better understood with reference to the following drawings. The components in the drawings are not necessarily to scale, emphasis instead being placed upon clearly illustrating the principles of the present invention. To facilitate illustrating and describing some parts of the invention, corresponding portions of the drawings may be exaggerated in size, e.g., made larger in relation to other parts than in an exemplary device actually made according to the invention. Elements and features depicted in one drawing or embodiment of the invention may be combined with elements and features depicted in one or more additional drawings or embodiments. Moreover, in the drawings, like reference numerals designate corresponding parts throughout the several views and may be used to designate like or similar parts in more than one embodiment.

DETAILED DESCRIPTION OF EMBODIMENTS

Embodiments will now be described with reference to the drawings, wherein like reference numerals are used to refer to like elements throughout. It will be understood that the figures are not necessarily to scale.

This specification describes novel a system and method to treat spinal fractures. Aspect of the present invention will be described with regard to the treatment of vertebral bodies, e.g., odontoid fractures. It should be appreciated, however, aspects of the present invention are not limited in their application to odontoid fractures. The systems and methods are applicable to the treatment of fractures in diverse bone types, including, but not limited to, such bones as the radius, the humerus, the femur, the tibia or the calcanus.

Figure 1:
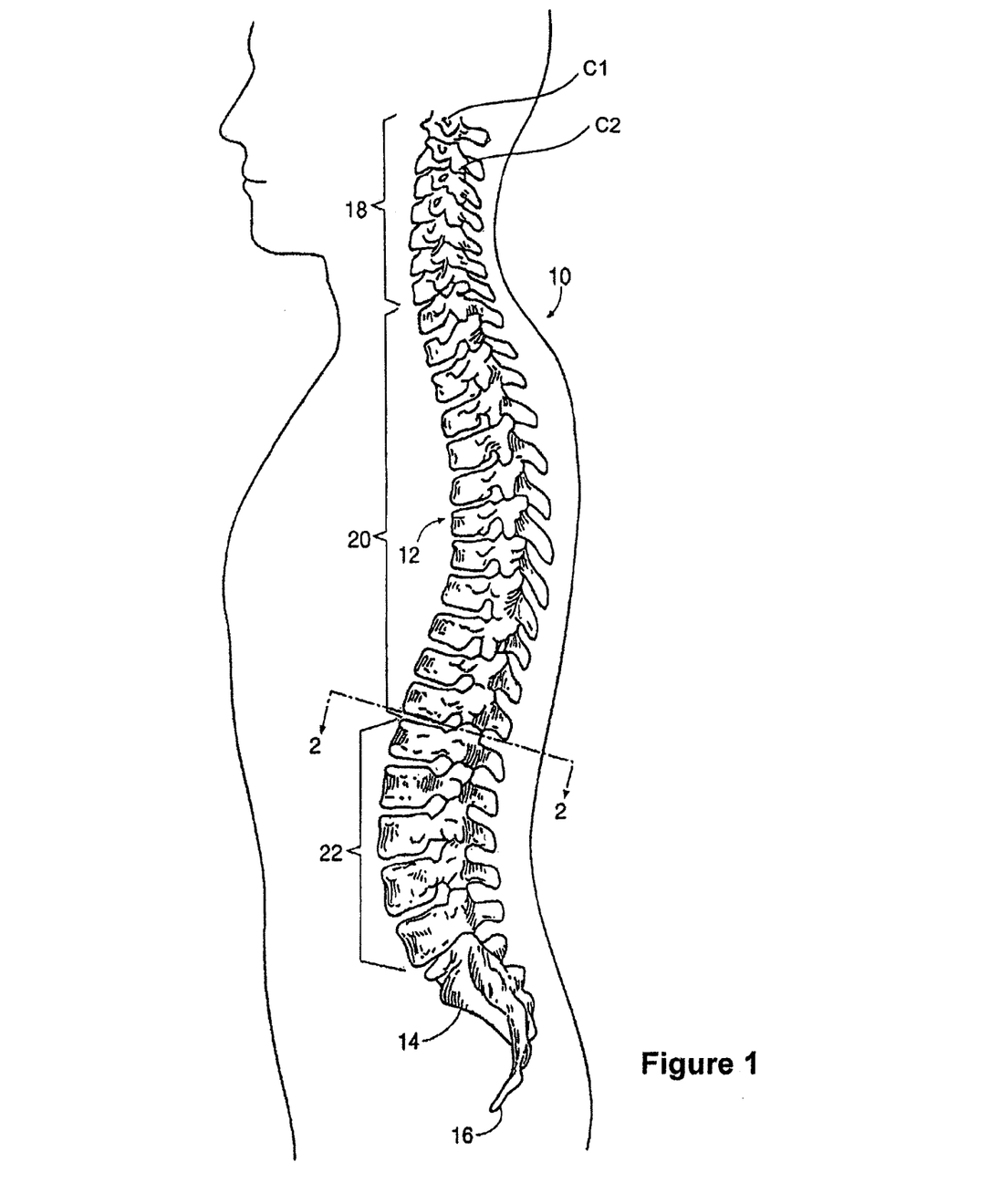
FIG. 1 is an exemplary lateral view of a human spine.
Figure 2:
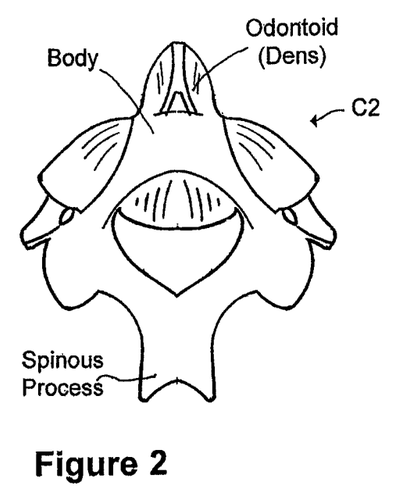
FIG. 2 is an exemplary cross-section view of a C2 vertebral body, which is the second cervical body of the spinal column illustrated in FIG. 1.

Referring to FIG. 1, an exemplary spinal column 10 of a human being is illustrated. The spinal column 10 includes a number of uniquely shaped bones, called vertebrae 12, a sacrum 14, and a coccyx 16 (also called the tail bone). The number of vertebrae 12 that make up the spinal column 10 depends upon the species of animal. In a human, there are twenty-four vertebrae 12, comprising seven cervical vertebrae 18, twelve thoracic vertebrae 20, and five lumbar vertebrae 22. Aspects of the present invention will be described with respect to the second cervical vertebra (C2) of the spine, as illustrated in FIG. 1. C2 forms the pivot upon which the first cervical vertebra C1 (the atlas), which carries the head, rotates. A distinctive characteristic of C2 bone is the strong odontoid process ("dens") (also referred to herein as "odontoid"), which rises perpendicularly from the upper surface of the body, as illustrated in FIG. 2 in cross-sectional view.

Figure 3:
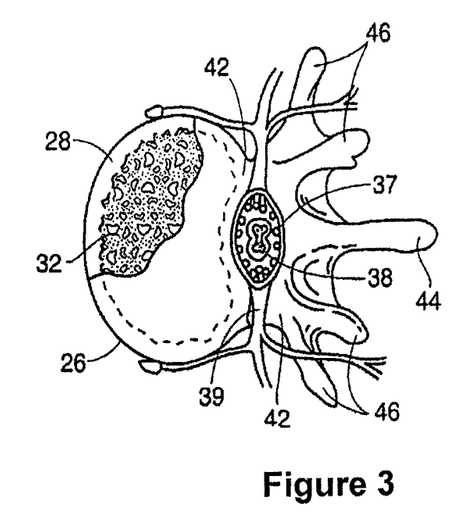
FIG. 3 is an exemplary coronal view of vertebral body, which is part of the spinal column illustrated in FIG. 1.
Figure 4:
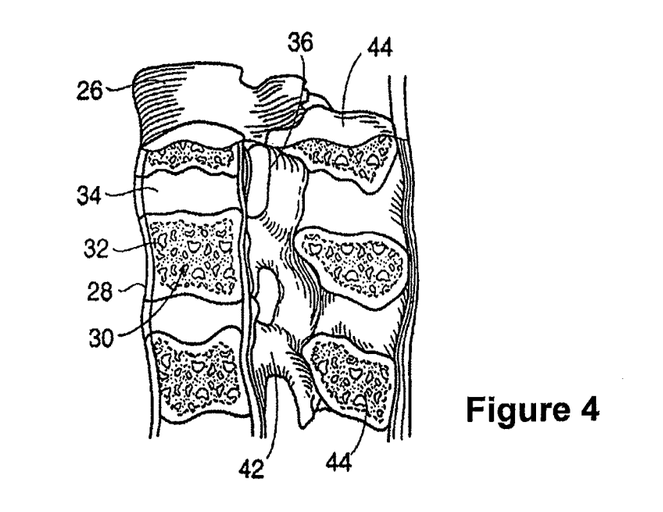
FIG. 4 is am exemplary coronal view of a plurality of vertebral bodies shown in FIG. 1.

When viewed from the side, as illustrated in FIG. 1, the spinal column 10 forms an S-shaped curve. The curve serves to support the head, which is heavy. As FIGS. 1, 3 and 4 illustrate, each vertebra 12 includes a vertebral body 26, which extends on the anterior (i.e., front or chest) side of the vertebra 12. The vertebral body 26 illustrated in FIGS. 3 and 4 is exemplary in nature and is provided solely for the purposes of illustration. The vertebral body 26 is generally in the shape of an oval disk. The vertebral body 26 includes an exterior formed from compact cortical bone 28. The cortical bone 28 encloses an interior volume 30 of reticulated cancellous, or spongy, bone 32 (also called medullary bone or trabecular bone). A "cushion," called an intervertebral disk 34, is located between the vertebral bodies 26.

An opening, called the vertebral foramen 36, is located on the posterior (i.e., back) side of each vertebra 12. The spinal ganglion 39 pass through the foramen 36. The spinal cord 38 passes through the spinal canal 37. The vertebral arch 40 surrounds the spinal canal 37. The pedicle 42 of the vertebral arch 40 adjoins the vertebral body 26. The spinous process 44 extends from the posterior of the vertebral arch 40, as do the left and right transverse processes 46.

The remaining disclosure will focus on a novel system and method to repair an odontoid fracture. As stated above, the system and method described herein may be applicable to other treatments.

Figure 5A:
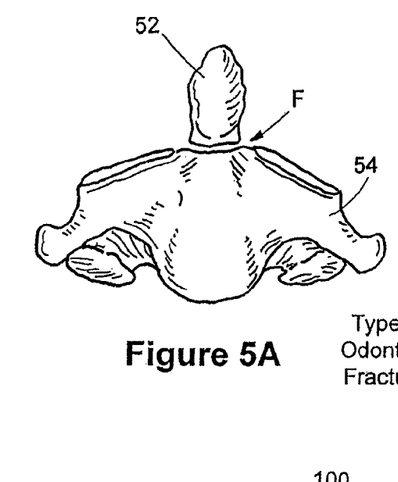
FIGS. 5A-5B illustrate anterior-posterior view and lateral view, respectively of an odontoid fracture in accordance with aspects of the present invention.
Figure 5B:
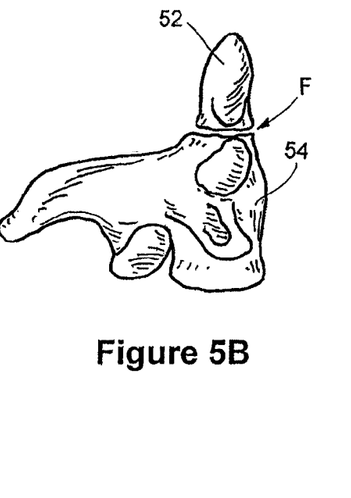

An exemplary type-2 odontoid fracture is illustrated in FIGS. 5A (anterior-posterior view) and 5B (a lateral view). A type-2 odontoid fracture often requires surgery. As illustrated in FIGS. 5A-5B, a type-2 odontoid fracture is a fracture (F) of the odontoid 52 from the C2 cervical body 54. A type-2 odontoid fracture generally occurs at the base of the odontoid 52 as it attaches to the body of C2 54. Options of treatment for type-2 odontoid fractures include: halo stabilization, C1-C2 fusion or internal fixation. Halo stabilization is often poorly tolerated by patients. C1-C2 fusion generally eliminates 50% of cervical rotation. Anterior screw fixation with single or dual cannulated screws is the typical internal fixation technique. Such method of fixation often does not provide adequate stabilization of the fracture secondary to poor fixation in the C2 body.

Figures 6, 7, 8:
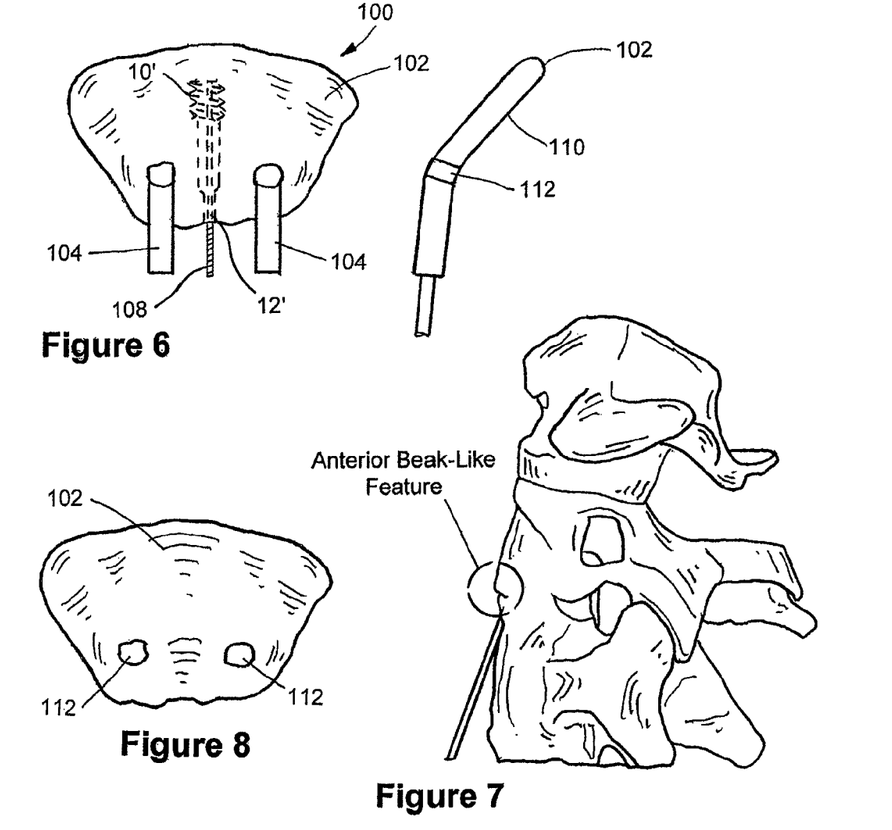
FIG. 6 is an exemplary fixation system in accordance with aspects of the present invention.
FIG. 7 is a lateral view of a plurality of vertebral bodies.
FIG. 8 is an exemplary perspective view of a surface of a fixation plate in accordance with aspects of the present invention.

A cervical fixation system 100 is illustrated in FIG. 6. The cervical fixation system 100 generally includes a plate 102, fastening devices 104 (e.g., fastening screws), a fixation device 106 (e.g., a lag screw), and a dynamic compression screw 108.

The plate 102 includes a plate surface 110 that may conform to at least a portion of a surface of a cervical body. The plate surface 10 is configured for fixation of the plate 102 to the cervical body. For example, the plate surface 110 may be designed to be applied to the anterior caudal portion of C2 body below the odontoid neck. In one embodiment, the plate 102 may be contoured to sit flush on the anterior inferior surface of the C2 body below the odontoid neck. Referring to FIG. 6, the plate 102 is contoured to the anterior beaklike surface of C2 body, which is illustrated in FIGS. 5B and 7. The plate 102 may be made of any suitable material. Suitable materials include, for example, medical grade stainless steel, cobalt chrome, titanium, ceramics, composite materials, epoxy materials, trabecular metal materials, and the like.

Figure 9:
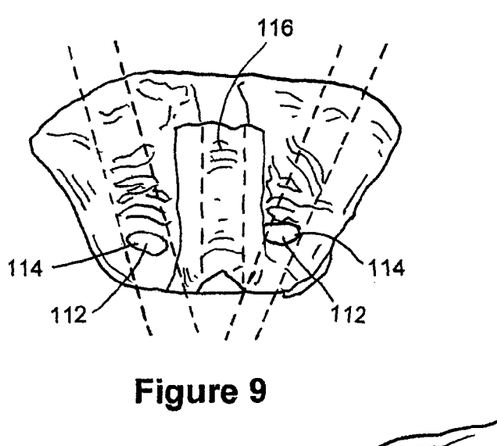
FIG. 9 is an exemplary perspective view of an opposing surface of the fixation plate illustrated in FIG. 8.

The plate 102 includes a plurality of voids 112 formed in the plate, as illustrated in FIG. 8. The voids 112 are positioned to allow fixation of the plate 102 to the cervical body. For example, the voids 112 may include one or more fixed angled locking screw holes formed in the body of the plate 102 for fixation of the plate onto the cervical body. In general, the voids 112 have threaded walls formed in the plate 102 to securely engage or lock fastening devices 104, which are used to secure the plate to the cervical body. In one embodiment, the voids 112 may be angled in a predetermined manner in an inferior to superior, medial to lateral orientation, as illustrated in FIG. 9, for example. In one embodiment, the voids are configured at an angle of 25-35 degrees anterior to posterior; and 5-15 degrees medial to lateral.

The voids 112 also may include threads 114 on the surface of the plate that creates the plate voids 112, as shown in FIG. 9. The threads 114 along the sides of the plate 102 that forms the voids 112 may be provided to lock in place fastening devices 104 (e.g., fixation screws) that have corresponding threads. The plate 102 may include a suitable number of voids 112 for securing the plate 102 to the cervical body. For example, two to four voids 112 may be a suitable number of voids to be used in conjunction with a fastener to secure the plate 102 to the cervical body.

Figure 10:
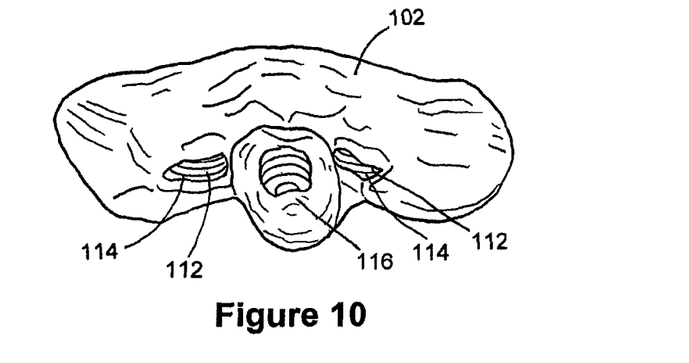
FIG. 10 is an exemplary top view of the fixation plate illustrated in FIG. 8.

As illustrated in FIG. 10, the plate 102 further includes a shaft 116 coupled to a posterior surface of the plate 102. Preferably, the shaft 116 may be formed in the plate 102 as an integral device (e.g., a one-piece construction). Alternatively, the shaft 116 may be separately attached to the plate 102. The shaft 116 may be substantially hollow to house the fixation device 106, as discussed below. The plate shaft 116 may have flattened lateral sides so as to block lag screw rotation within the posterior plate shaft 116, as shown in FIG. 10. Generally, the shaft 116 is made of the same material as the plate 102. Alternatively, the shaft 116 may be made of a different material than the plate 102.

As stated above, the cervical fixation system 100 includes fastening devices 104. The fastening devices 104 are configured to be received by at least one void 112 formed in the plate. Generally, each void 112 is configured to receive a separate fastening device 104, which are used to secure the plate 102 to the cervical body. One of ordinary skill in the art will readily appreciate that not all of the voids 112 will require a fastening device 104 to secure the plate 102 to the cervical body. For example, one or more voids 112 may not be used to secure the plate 102 to the cervical body.

In one embodiment, fastening devices 104 may be medical grade screws. For example, the first fastening device 104 may be in the form of a locking screw (e.g., a titanium cannulated or non-cannulated threaded bone screw with a locking head). As noted above, the system 100 may include any number of fastening devices 104 in order to adequately secure the plate 102 to the cervical body. For example, the system 102 may include one or more pairs of voids 112, which may receive fastening devices 104. The fastening devices 104 may include at least one locking screw that locks into a void 112 on the plate 102.

Figure 11:
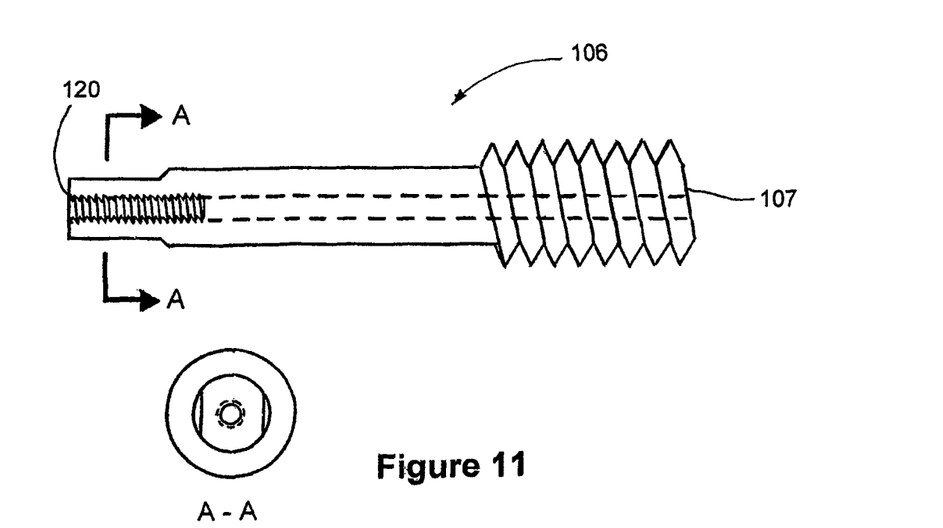
FIG. 11 is an exemplary plan view and cross-sectional view of a fixation device in accordance with aspects of the present invention.

The cervical fixation system 100 also includes a fixation device 106 (e.g., a lag-type fixation device). An exemplary fixation device 106 is illustrated in FIG. 11. The fixation device 106 is configured to be housed in the plate posterior shaft 116 of the plate 102. The fixation device 106 may be further configured to extend through the shaft 116 and be secured across at least a portion of the cervical body 54 and the odontoid 52. In one embodiment, the fixation device 106 is a headless 4.5-5.5 millimeter partially threaded cancellous type lag screw. The length of the fixation device 106 (e.g., lag screw) may vary between 25-40 millimeters, for example. In one embodiment, the lag screw is fully cannulated and houses a guide wire. The guide wire may have a diameter of 0.25 to 0.5 mm, for example. As shown in FIG. 11, the lower end of the fixation device 106 includes flattened lateral sides that correspond to the flattened lateral sides of the post 116 discussed above.

The cannulated center portion of fixation device 106 may be threaded to accept a compression screw 108 at the caudal end 120, as shown in FIG. 11. Threading the small compression screw into the lower end of the lag screw will pull the lag screw caudal into the plate 102, which provides compression at the fracture site, as illustrated in FIGS. 21A and 21B, as discussed below. The lag screw is designed to slide cephalad and caudal within the shaft 116.

The compression screw 108 may be inserted though the fixation device 106 into the lower or caudal end of the fixation device 106. When tightened, the compression screw 108 applies a compression force across at least a portion of the cervical body and an odontoid associated with the cervical body to securely fix the odontoid to the cervical body.

Figure 12:
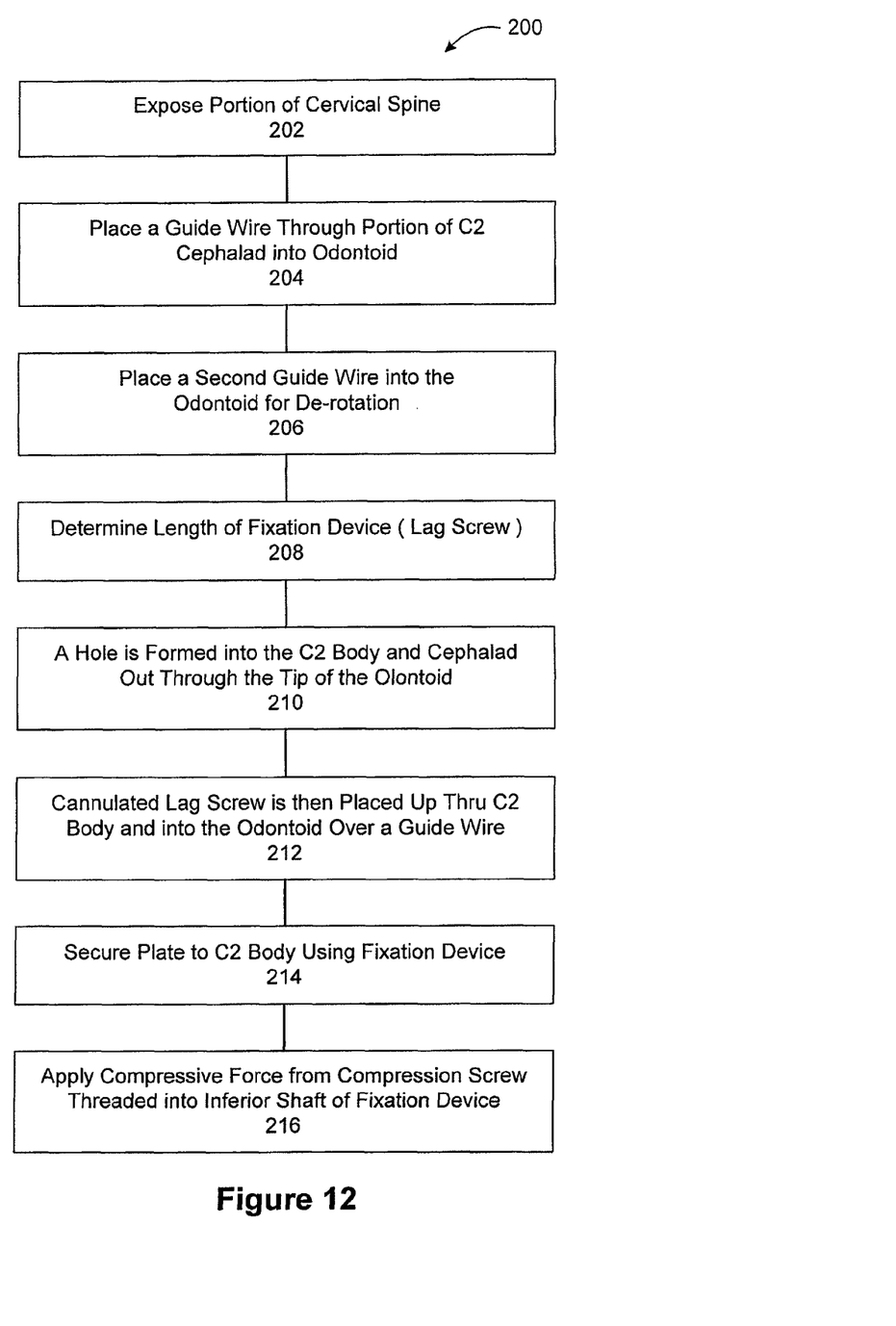
FIG. 12 is an exemplary method in accordance with aspects of the present invention.

Aspects of the invention further relate to a method 200 for installing the cervical fixation system 100 in an associated patient. Referring to FIG. 12, at block 202, at least a portion of a cervical spine of an associated patient is exposed to reveal the vertebral body to be repaired. Access to the vertebral body can be accomplished from many different directions, depending upon the targeted location within the vertebral body, the intervening anatomy, and the desired complexity of the procedure. For example, access can also be obtained through a pedicle 42 (transpedicular), outside of a pedicle (extrapedicular), along either side of the vertebral body (posterolateral), laterally or anteriorly. In addition, such approaches can be used with a closed, minimally invasive procedure or with an open procedure.

In a preferred embodiment, the patient may be placed in the supine position with the patient's head secured by tongs or some other device or mechanism to allow reduction of the fracture. Single and/or biplane fluoroscopy may be used to guide reduction of the fracture and/or for placement of one or more components of the cervical fixation system 100. An anterior exposure to the cervical spine is performed in one embodiment. For example, a left or right incision, depending on the surgeon's preference, is made longitudinally, inferior to the body of C2. Such an incision has been found to allow proper angulation of the guide wires, the fixation device 106 (e.g., a lag screw) and fastening devices 104.

Figure 13A:
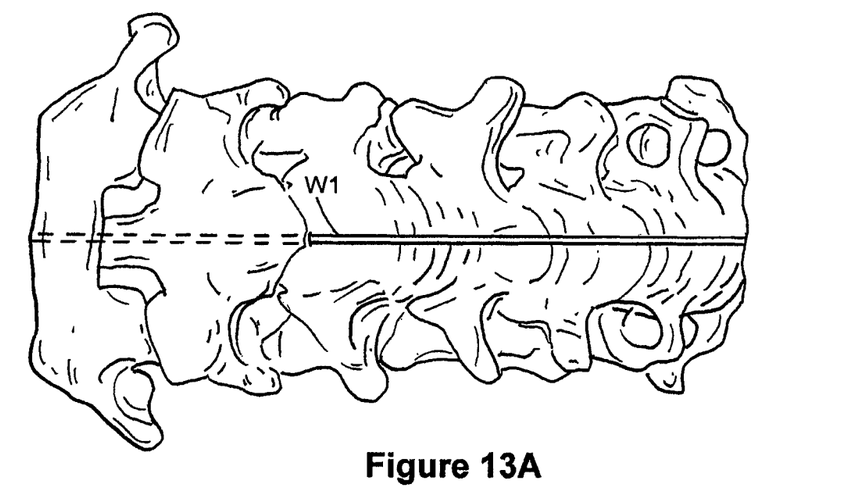
FIGS. 13A and 13B illustrate insertion of a guide wire in accordance with aspects of the present invention.
Figure 13B:
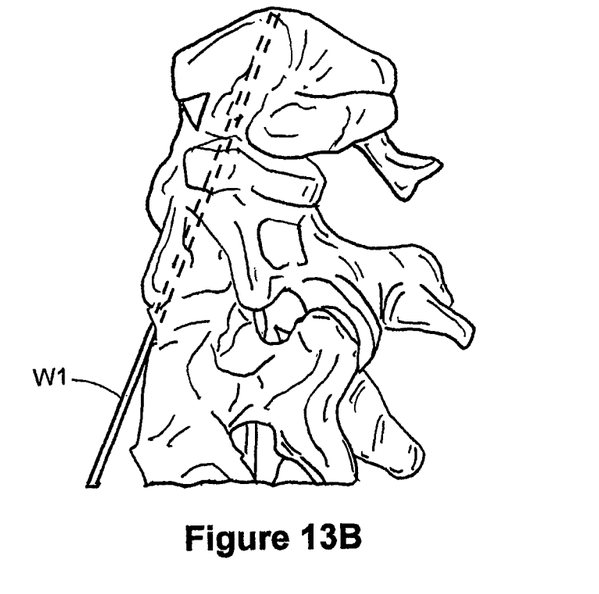

At block 204, a guide wire (W1) is placed through a portion of C2 cephalad into the odontoid, as shown in FIGS. 13A and 13B. A C-arm guide or other such device may be used for precise placement of the guide wire into the odontoid.

At block 206, a second guide wire (W2) may be placed in the odontoid in order to allow for de-rotation or adjusting of the fractured odontoid. The second guide wire W2 may be used to allow a surgeon to adjust alignment of the odontoid to an anatomically desired position.

At block 208, a length determination is made to determine how long the fixation device should be to secure the odontoid to the C2 body. In one embodiment, a depth gauge is placed over the guide wire W1 discussed above with respect to block 204. One of ordinary skill in the art will appreciate that the length of the fixation device may be determined in a variety of ways (e.g., X-rays, CT scans, measuring without the guide wire, etc.).

Figure 14A:
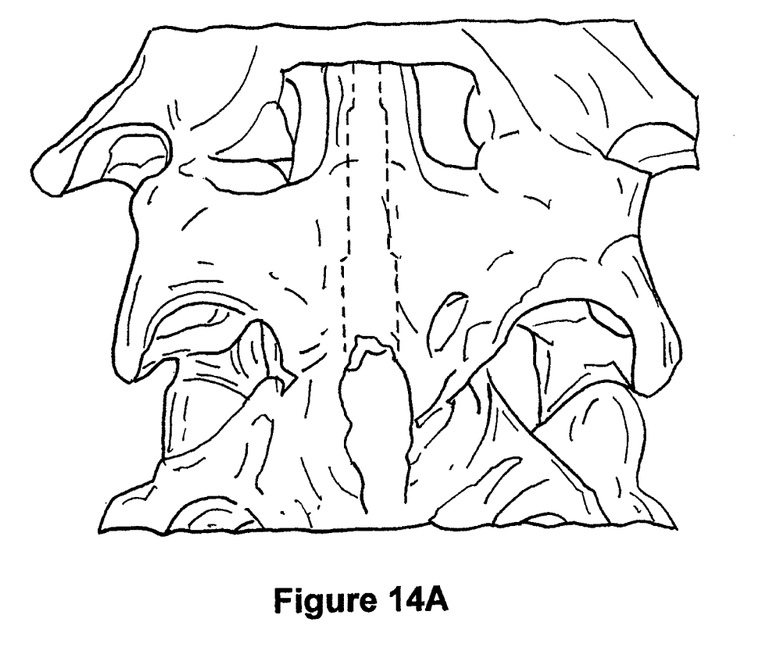
FIGS. 14A and 14B illustrate coring out portion of the C2 vertical body in accordance with aspects of the present invention.
Figure 14B:
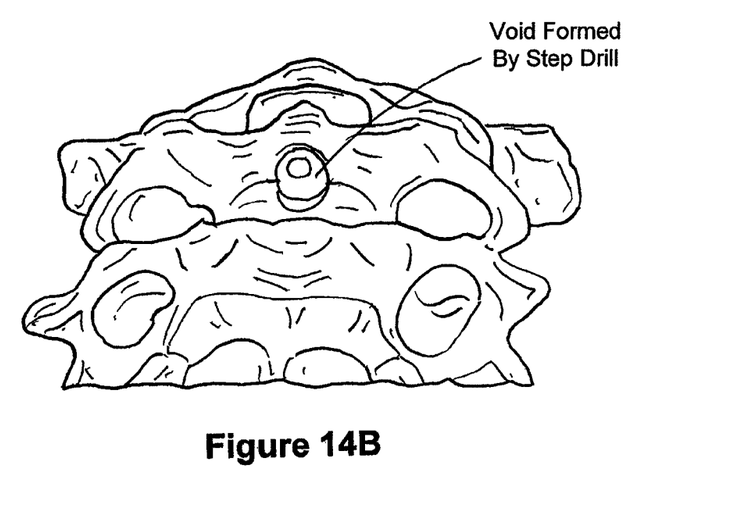

At block 210, a hole is drilled in a caudal to cephalad direction out of the tip of the odontoid over the guide wire W1 with the wider step of a cannulated drill coring out the anterior inferior beak of the C2 body, as shown in FIGS. 14A and 14B. In one embodiment, the hole is approximately 2.5 to 4.0 mm, with the caudal portion of the hole large enough to house the plate posterior shaft 116. One of ordinary skill in the art will appreciate that the disclosed diameter is exemplary in nature and any suitable diameter is within the scope of the present disclosure. The cannulated adjustable step drill is adjusted to the length determined by the measurement made in block 208. As shown in FIG. 14A, the hole is wider at bottom portion than bottom portion of FIG. 14A due to use of step drill.

Figure 15A:
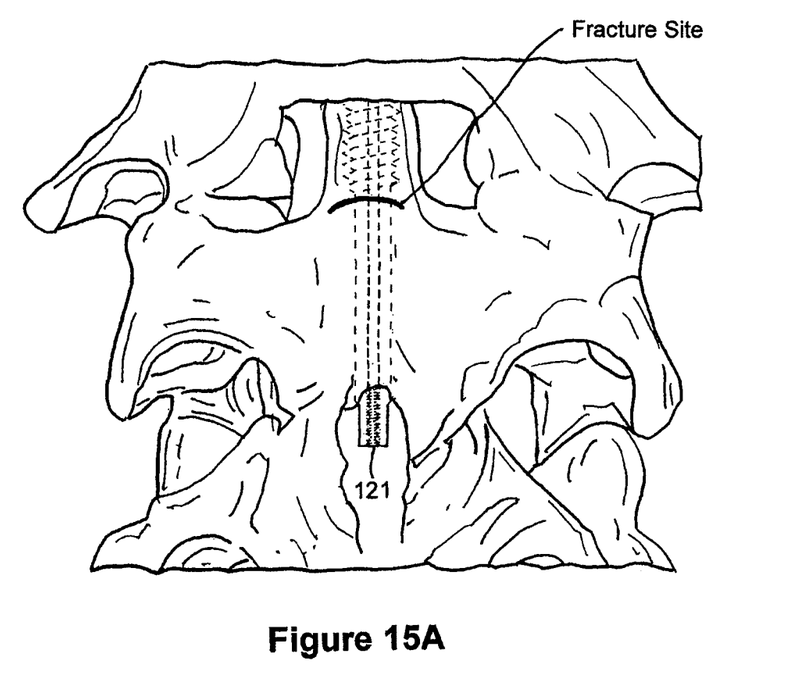
FIGS. 15A and 15B illustrate exemplary positioning of the fixation device in the odontoid in accordance with aspects of the present invention.
Figure 15B:
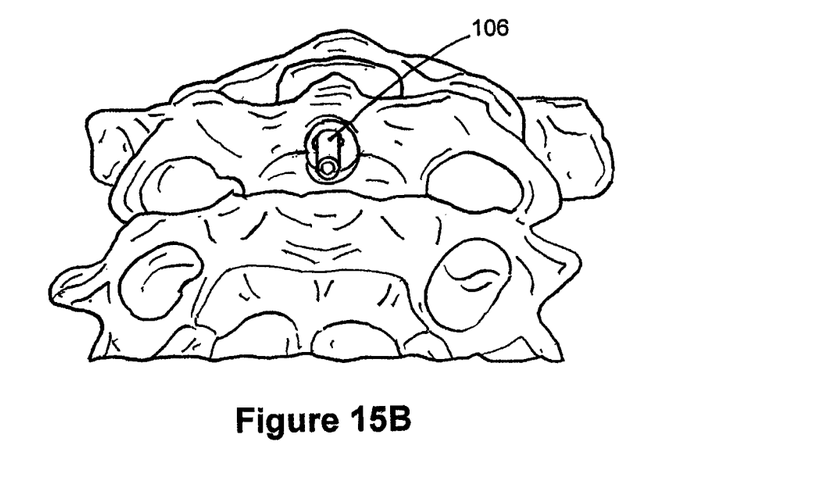
Figure 16A:
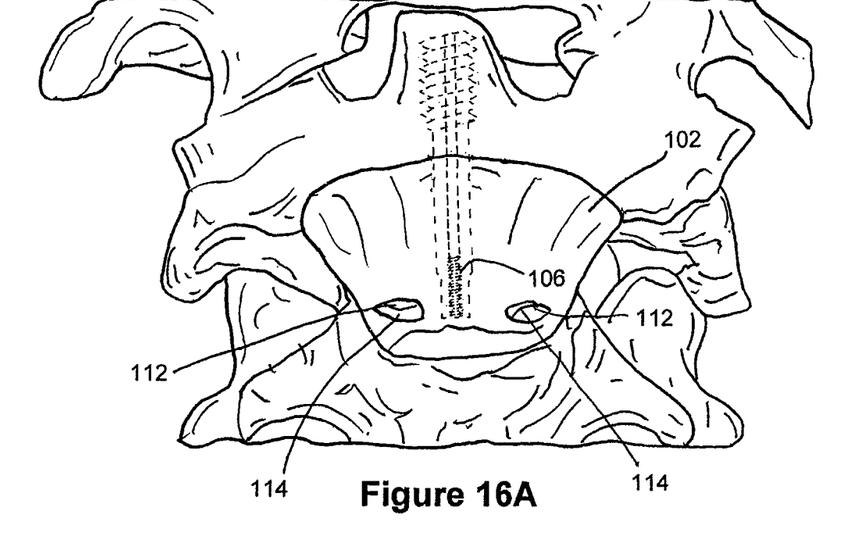
FIGS. 16A, 16B, 17A and 17B provide exemplary illustrations of the plate being secured in such a manner that the fixation device lag screw is aligned with shaft of the plate in accordance with aspects of the present invention.
Figure 16B:
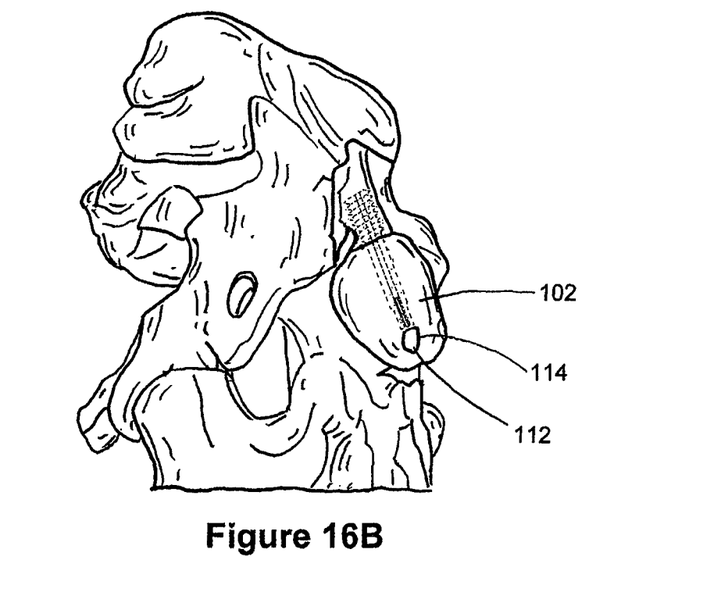
Figure 17A:
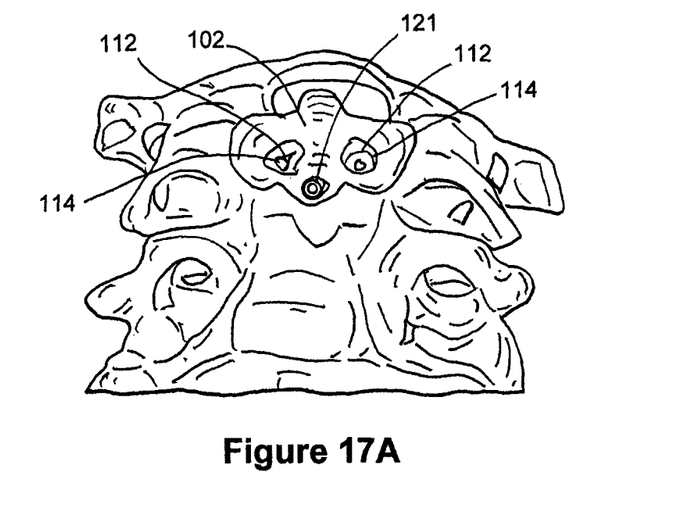
Figure 17B:
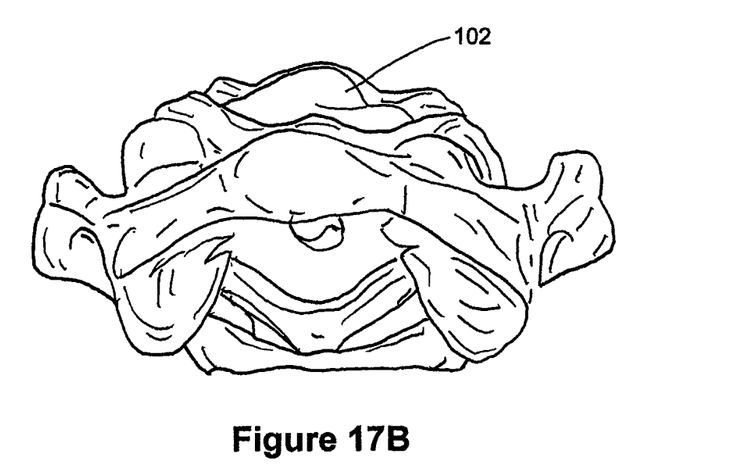
Figure 18A:
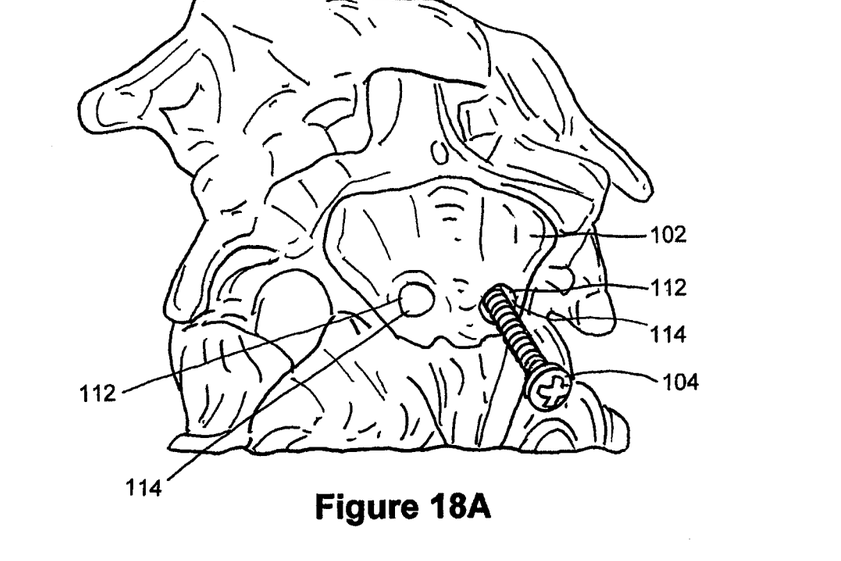
FIGS. 18A, 18B, 19A and 19B provide exemplary illustrations of plate being secured to a vertebral body in accordance with aspects of the present invention.
Figure 18B:
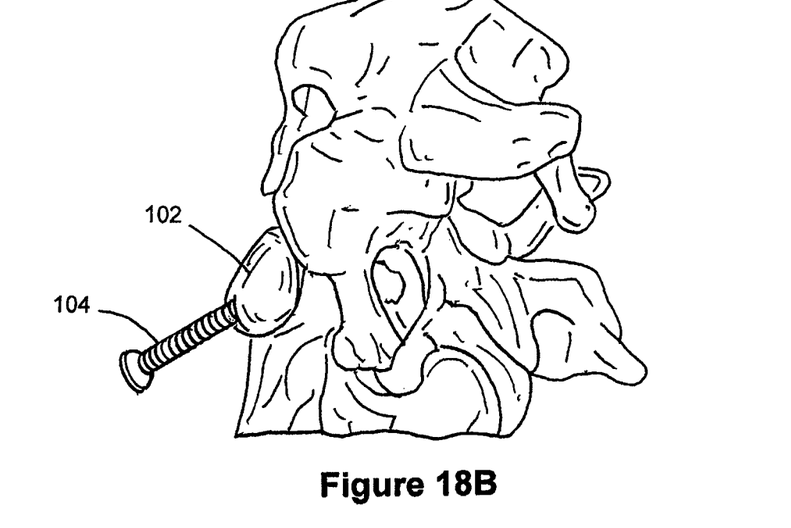
Figure 19A:
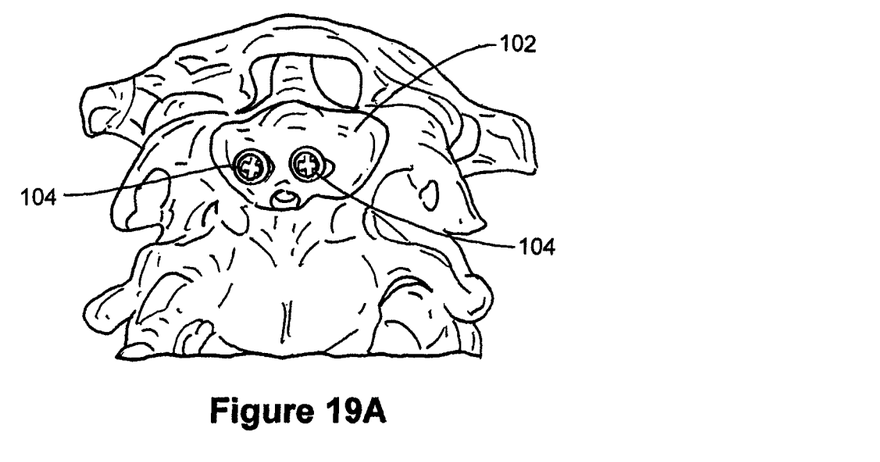
Figure 19B:
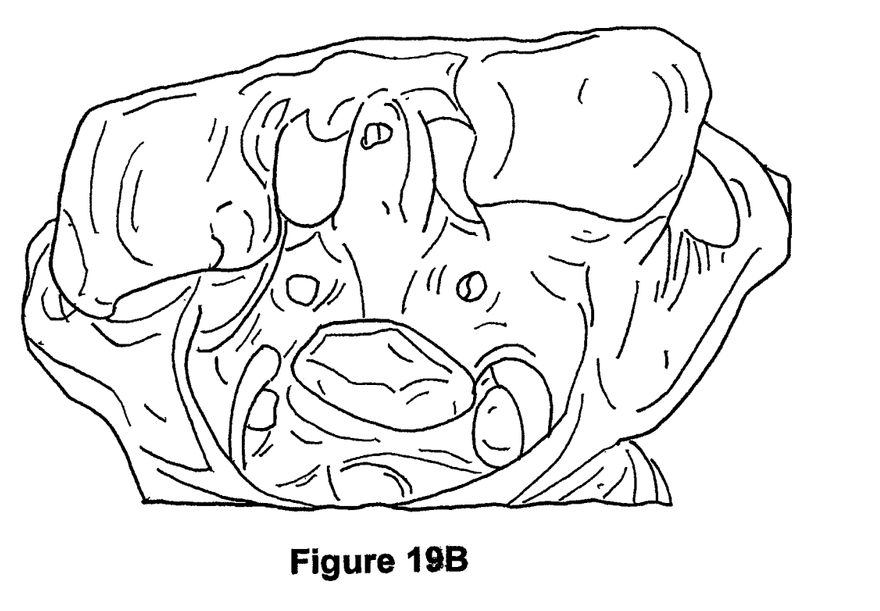

At block 212, a cannulated lag screw (also referred to herein as the fixation device 106) is placed into the odontoid over the guide wire W1. In one embodiment, the lag screw is headless so as to allow the lag screw to be secured within the shaft 116. Once the lag screw is inserted and properly positioned, the guide wire W1 may be removed. However, preferably the guide wire is not kept in place until the plate 102 is in place. FIGS. 15A and 15B illustrate positioning of the lag screw in the odontoid. Generally, the plate 102 is slid over the guide wire (W1) to make it easier to position the plate 102.

At block 214, the anterior plate 102 is secured onto the C2 inferior body. As discussed above, the plate 102 includes a plate surface that conforms to at least a portion of a surface of a cervical body surface of the associated patient's cervical spine. In addition, the plate includes a plurality of voids 112 formed in the plate, wherein the voids are positioned to allow fixation of the plate to the cervical body and the plate further includes a shaft 116 coupled to a posterior surface of the plate. The plate 102 is secured in such a manner that the lag screw is aligned with the shaft, as illustrated in FIGS. 16A, 16B and 17A, 17B. The plate 102 is secured to the C2 body through the one or more voids 112 with one or more fastening devices 104, as discussed above and illustrated in FIGS. 18A, 18B and 19A, 19B.

Figure 20A:
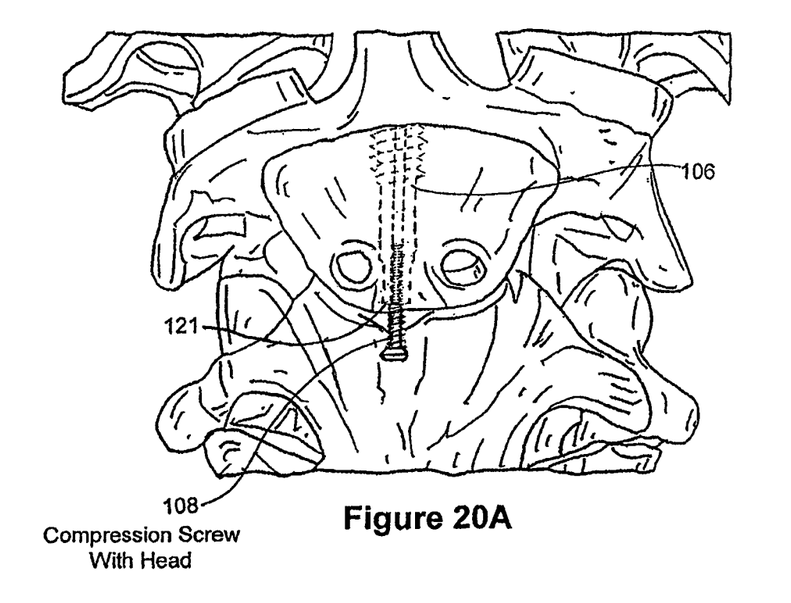
FIGS. 20A and 20B provide an exemplary illustration of the lag screw pulled in a caudal direction through the shaft to apply a compressive the odontoid with the C2 body in accordance with aspects of the present invention.
Figure 20B:
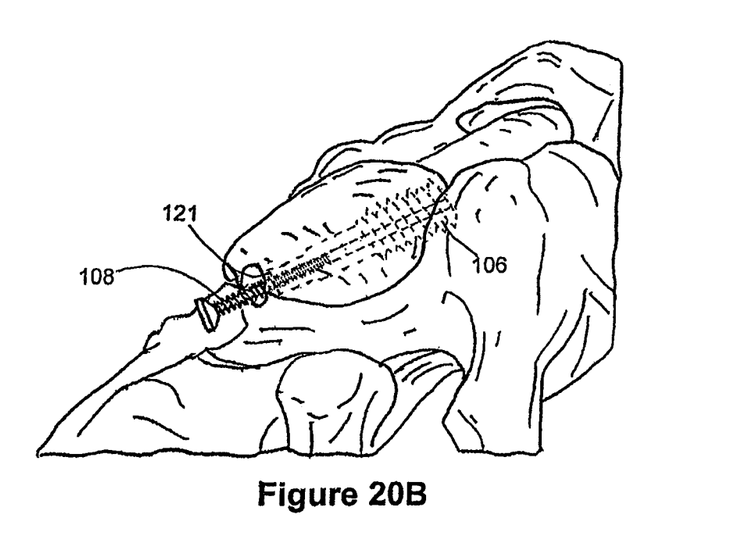

At block 216, a compressive force is applied from a compression screw threaded into an inferior shaft of the lag screw, wherein as the head of the compression screw 108 contacts an inferior edge of the anterior plate, the lag screw is pulled in a caudal direction through the shaft to apply a compressive force across the odontoid fracture, as shown in FIGS. 20A and 20B.

Unless otherwise defined, the method steps described above can be executed either contemporaneously or sequentially in many combinations or orders of execution. Specifically, the ordering of the flowchart diagram is not to be considered as limiting. For example, two or more method steps, appearing in the following description or in the flowchart diagrams in a particular order, can be executed in a different order (e.g., a reverse order) or substantially contemporaneously. Additionally, unless expressly claimed, several method steps described above are optional and may not be executed.

Although certain embodiments have been shown and described, it is understood that equivalents and modifications falling within the scope of the appended claims will occur to others who are skilled in the art upon the reading and understanding of this specification.

What is claimed is:

1. A cervical fixation system comprising:
    a plate including a plate surface for fixation to a surface of a cervical body, wherein the plate includes a plurality of voids formed in the plate, wherein the voids are positioned to allow fixation of the plate to the cervical body and the plate further includes a shaft coupled to a posterior surface of the plate;
    a first fastening device and a second fastening device, wherein the first and second fastening devices are configured to be received by one or more voids formed in the plate, wherein the fastening devices are configured to secure the plate to the surface of the cervical body; and
    a fixation device configured to be housed in the shaft, wherein the fixation device is configured to be secured across at least a portion of the cervical body and an odontoid of the cervical body and the fixation device includes a compression screw to apply a compression force across at least a portion of the cervical body and the odontoid of the cervical body;
    wherein the first fastening device and the second fastening device are configured to be attached to the same cervical body having the odontoid to which the fixation device is secured across.

2. The system of claim 1, wherein the voids formed in the plate are angled in an inferior to superior and a medial to lateral orientation.

3. The system of claim 2, wherein at least one of the voids includes a first end having a threaded portion to lock in place the first fastening device or second fastening device.

4. The system of claim 1, wherein the first fastening device includes at least one 25 locking screw.

5. The system of claim 1, wherein the shaft is formed in the plate.

6. The system of claim 1, wherein the shaft is attached to the plate.

7. The system of claim 1, wherein the fixation device further includes a cannulated and headless lag screw.

8. The system of claim 7, wherein the cannulated lag screw is configured to receive the compression screw.

9. The system of claim 7, wherein the compression screw is housed within the 10 fixation device.

10. The system of claim 1, wherein the shaft includes flattened lateral sides to block rotation of a lag screw within the posterior shaft.

11. The system of claim 1, wherein the plate is configured to contour an anterior surface of a C2 cervical body that is below a neck associated with the odontoid.

12. The system of claim 1, wherein the shaft is configured to allow a lag screw to slide in a cephalad direction and a caudal direction within the posterior plate.

13. The system of claim 12, wherein the lag screw has a cannulated center portion having one or more threads to accept the compression screw at a caudal end of the lag screw.

* * * * *